United States Patent
Rovison, Jr. et al.

(10) Patent No.: US 9,018,142 B2
(45) Date of Patent: *Apr. 28, 2015

(54) OIL-FIELD BIOCIDE METHOD UTILIZING A PERACID

(75) Inventors: John M. Rovison, Jr., Sanborn, NY (US); Shurong Huang, Houston, TX (US); Henry A. Pfeffer, Mercerville, NJ (US)

(73) Assignee: PeroxyChem LLC, Philadelphia, PA (US)

( * ) Notice: Subject to any disclaimer, the term of this patent is extended or adjusted under 35 U.S.C. 154(b) by 615 days.

This patent is subject to a terminal disclaimer.

(21) Appl. No.: 12/632,056

(22) Filed: Dec. 7, 2009

(65) Prior Publication Data

US 2010/0160449 A1   Jun. 24, 2010

Related U.S. Application Data

(60) Provisional application No. 61/203,078, filed on Dec. 18, 2008.

(51) Int. Cl.
| | |
|---|---|
| *C09K 8/68* | (2006.01) |
| *A01N 37/02* | (2006.01) |
| *C09K 8/12* | (2006.01) |
| *C09K 8/60* | (2006.01) |

(52) U.S. Cl.
CPC . *C09K 8/68* (2013.01); *A01N 37/02* (2013.01); *C09K 8/12* (2013.01); *C09K 8/605* (2013.01)

(58) Field of Classification Search
CPC ............ C09K 8/68; C09K 8/12; C09K 8/605; C09K 8/588; A01N 37/02; A01N 2300/00
USPC ........... 210/749, 759, 764; 507/200, 204, 219
See application file for complete search history.

(56) References Cited

U.S. PATENT DOCUMENTS

| | | | |
|---|---|---|---|
| 2,347,434 A | 4/1944 | Reichert et al. | |
| 2,590,856 A | 4/1952 | Greenspan et al. | |
| 2,609,391 A | 9/1952 | Greenspan et al. | |
| 3,254,719 A | 6/1966 | Root | |
| 3,329,610 A | 7/1967 | Kreuz et al. | |
| 3,470,959 A | 10/1969 | Kreuz et al. | |
| 4,152,274 A | 5/1979 | Phillips et al. | |
| 4,152,275 A | 5/1979 | Horodysky et al. | |
| 4,552,591 A | 11/1985 | Millar | |
| 4,995,461 A | 2/1991 | Sydansk | |
| 5,069,286 A | 12/1991 | Roensch et al. | |
| 5,268,112 A | 12/1993 | Hutchins et al. | |
| 6,001,158 A | 12/1999 | Elphingstone et al. | |
| 6,627,657 B1 * | 9/2003 | Hilgren et al. | 514/553 |
| 6,764,981 B1 * | 7/2004 | Eoff et al. | 507/110 |
| 6,818,594 B1 | 11/2004 | Freeman et al. | |
| 7,156,178 B2 | 1/2007 | Rae et al. | |
| 7,256,160 B2 | 8/2007 | Crews | |
| 2006/0009363 A1 | 1/2006 | Crews | |
| 2007/0284101 A1 | 12/2007 | Valeriano et al. | |

FOREIGN PATENT DOCUMENTS

| | | |
|---|---|---|
| EP | 0 563 584 B1 | 9/1995 |
| GB | 925373 | 5/1960 |
| RU | 2 249 097 C2 | 3/2005 |
| RU | 2005 141 435 A | 6/2006 |
| WO | WO 96-14092 | 5/1996 |
| WO | WO 00-04777 | 2/2000 |
| WO | WO 01-02698 A1 | 1/2001 |
| WO | WO 85-04213 A1 | 9/2004 |

OTHER PUBLICATIONS

Dow Glutaraldehyde Performance Advantages in Oilfield Applications Mar. 2007.
Dow Ucaricide Antimicrobials for Oilfield Applications—Glutaraldehyde Oct. 2004.
FMC Peracetic Acid 15% 15-10 Technical Data Sheet.
FMC Peracetic Acid 35% 35-6 Technical Data Sheet.
Persan 15% Peracetic Acid Technical Data Sheet 070605.
Persan A 6% Peracetic Acid Technical Data Sheet 070605.
Kitts M. "Disinfection of Wastewater with Peracetic Acid: A Review", Environment International 30 (2004) pp. 47-55.

\* cited by examiner

*Primary Examiner* — Sreeni Padmanabhan
*Assistant Examiner* — Shobha Kantamneni
(74) *Attorney, Agent, or Firm* — Duane Morris LLP

(57) ABSTRACT

Aqueous well treatment fluid compositions with biocidal activity are disclosed comprising a polymer for modifying fluid viscosity in the aqueous fluid, an organic monocarboxylic peracid being present in an anti-microbial amount of about 1 ppm to about 1000 ppm, and a controlled amount of hydrogen peroxide also being present. Peracetic acid is the preferred peracid. The viscosity-modifying polymer in the aqueous well treatment fluid composition may serve to reduce friction in the fluid or increase fluid viscosity. A method of using such compositions is also disclosed.

11 Claims, No Drawings

OIL-FIELD BIOCIDE METHOD UTILIZING A PERACID

FIELD OF THE INVENTION

The present invention relates to a biocide for aqueous fluids used in oil- and gas-field operations. More particularly, the invention relates to a peracetic acid biocide and method useful in oil- and gas-field applications.

BACKGROUND OF THE INVENTION

Peracetic acid, sometimes called peroxyacetic acid or PAA, is a well known chemical for its strong oxidizing potential. Peracetic acid has a molecular formula of $C_2H_4O_3$ or $CH_3COOOH$, a molecular mass of 76.05 g/mol, and a molecular structure as follows:

(1)

Peracetic acid is a liquid with an acrid odor and is normally sold in commercial formulations as aqueous solutions typically containing, e.g., 5, 15 or 35 wt % peracetic acid. Such aqueous formulations not only contain peracetic acid but also significant concentrations of hydrogen peroxide and acetic acid, in a dynamic chemical equilibrium.

Aqueous solutions of peracetic acid, diluted to concentrations below 5 wt % peracetic acid, are widely used in a variety of end use applications for their wide spectrum antimicrobial and biocidal properties, as bactericides, fungicides, disinfectants and sterilants, and also for their bleaching properties. Aqueous peracetic acid exhibits antimicrobial activity that is more potent than aqueous hydrogen peroxide at equivalent low concentrations. A good overview of peracetic acid and its commercial antimicrobial applications is given by M. Kitis in "Disinfection of wastewater with peracetic acid: a review" *Environment International* 30 (2004) 47-55.

Aqueous peracetic acid solutions have had limited use in commercial well drilling operations, and only a few uses in this application are described in the literature.

Peracetic acid has been described as a bactericide for use in water, called flood waters, used in secondary oil recovery, in U.S. Pat. No. 3,329,610 of Kreuz et al., the disclosures of which are hereby incorporated by reference. Besides the peracetic acid bactericide, the only other component present in the flood waters is a standard corrosion inhibitor, e.g., a mixture of fatty acid alkylolamide, amine sulfonate, glycerine and diethanolamine sulfonate (Example 3).

Another use for peracetic acid is well cleaning described in U.S. Pat. No. 3,470,959 of Kreuz et al., where peracetic acid is added to water (normally potable water) that is injected into so-called recharge wells that are used in conjunction with the removal of potable water from coastal underground potable water basins.

Peroxyacetic acid used in synergistic combination with a phosphonium salt compound has been described as an antimicrobial combination, in PCT International Patent Publication No. WO 2000/04777 of ECC International, primarily for use in industrial water treatments such as pulp and paper or cooling tower operations. The synergistic antimicrobial combination is described as being generally useful in a broad spectrum of end use applications, one of which mentioned is controlling microorganism contamination in oil-field drilling fluids and muds, and in secondary petroleum recovery processes (pages 4-5).

In another application in oil and gas well operations, peracetic acid and hydrogen peroxide are described as useful, in buffered solutions, for improving the permeability of wells containing polymer deposits by removing the polymer deposits, in U.S. Pat. No. 7,156,178 of Rae et al.

The use of buffered peracetic acid solutions of Rae et al. in U.S. Pat. No. 7,156,178 for removing polymer deposits underscores an apparent disadvantage of using peracetic acid as a biocide in commercial oil- and gas-field operations. Commercial peracetic acid solutions also contain significant concentrations of hydrogen peroxide, a strong oxidizer, which can degrade useful polymer additives also present in aqueous fluids used in commercial well drilling, recovery or production applications.

Several biocides are currently used in oil- and gas-field operations, the most commonly used being glutaraldehyde (also called 1,5-pentanedial) and tetrakis hydroxymethyl phosphonium sulfate (often abbreviated as THPS).

In oil- and gas-field operations, polymer additives have been widely used for decades to enhance or modify the characteristics of the aqueous fluids used in well drilling, recovery and production applications.

One example of such use is for friction reduction in water or other water-based (aqueous) fluids used for hydraulic fracturing treatments in subterranean well formations. Hydraulic fracturing creates fluid-conductive cracks or pathways in the subterranean rock formations in gas- and/or oil-producing zones, improving permeability of the desired gas and/or oil being recovered from the formation via the wellbore.

"Slick water" fluids are water or other aqueous fluids that typically contain a friction-reducing agent to reduce frictional drag and improve the flow characteristics of the aqueous fluid being pumped via the well into the gas- and/or oil-producing zones, whether for fracturing or other treatments. The friction reduction agents are usually polymers, and the most commonly used for this purpose are polyacrylamide polymers and copolymers. These friction-reducing additives allow the water to be pumped into the formation more quickly.

Another example of polymeric agents' utility in oil- and gas-field well applications is for viscosity enhancement. Many aqueous fracturing fluids utilize natural or synthetic viscosity-increasing polymers, some of which are categorized as gelling agents. Examples of such natural and synthetic polymer additives in fracturing fluids include guar, xanthan, cellulose derivatives and polyacrylamide and polyacrylate polymers and copolymers, and the like. The gel-forming or thickening additives allow the aqueous well fluid to carry a significant amount of a proppant, typically an inorganic solids propping agent like sand, into the fractures and fissures in the formation without premature settling of the proppant.

The present invention provides a peracetic acid biocide that is useful in aqueous fluids for oil- and gas-field operations and that is not deleterious to the viscosity-modifying polymer additives present in such aqueous treatment fluids.

BRIEF SUMMARY OF THE INVENTION

One aspect of the present invention is an aqueous well treatment fluid composition with biocidal activity comprising a polymer or copolymer for modifying fluid viscosity; an organic monocarboxylic peracid in an antimicrobial amount of about 1 ppm to about 1000 ppm; and hydrogen peroxide, the hydrogen peroxide concentration being less than the peracid concentration; in an aqueous medium.

Another embodiment of the invention is an aqueous well treatment fluid composition with biocidal activity comprising a fluid viscosity-reducing polymer or copolymer in a friction-reducing amount to provide improved fluid flow characteristics; peracetic acid in an antimicrobial amount of about 1 ppm to about 1000 ppm; and hydrogen peroxide, the hydrogen peroxide concentration being less than the peracetic acid concentration; in an aqueous medium.

Yet another embodiment of the invention is an aqueous well treatment fluid composition with biocidal activity comprising a viscosity-increasing polymer or copolymer in an amount sufficient to increase fluid viscosity; peracetic acid in an antimicrobial amount of about 1 ppm to about 1000 ppm; and hydrogen peroxide, the hydrogen peroxide concentration being less than the peracetic acid concentration; in an aqueous medium.

Still another embodiment of the present invention is a method of providing biocidal activity in a well treatment fluid comprising introducing, into an aqueous well treatment fluid composition comprising a polymer or copolymer for modifying fluid viscosity, and an aqueous monocarboxylic peracid solution in an antimicrobial-effective amount of about 1 ppm to about 1000 ppm, the aqueous peracid solution having a peracid acid weight concentration in excess of hydrogen peroxide also present in the aqueous peracid solution; and thereafter directing the aqueous well treatment fluid into a subterranean environment.

DETAILED DESCRIPTION OF THE INVENTION

The present invention is directed to peracids, and peracetic acid in particular, that are highly suitable for use as biocide formulations in aqueous well treatment fluids that are used in various aspects of subterranean oil- and gas-field well operations.

Aqueous well treatment fluids often contain polymer or copolymer additives that function to modify the viscosity characteristics of the aqueous well fluid, whether to reduce fluid viscosity {to reduce flowing friction and enhance fluid flow characteristics) or to increase fluid viscosity to provide a more viscous, thickened or partially gelled fluid (to maintain solid additives present in the fluid in suspension during well process operations). These aqueous well treatment fluids are used in subterranean locales for various functions, in well boreholes, in oil- or gas-bearing underground formations, or like subterranean environments.

The peracetic acid and other peracid biocides of this invention provide extremely effective control of microorganisms present in aqueous well treatment fluids containing viscosity-modifying polymers but without adversely affecting the functional properties of the viscosity-modified polymer-containing aqueous well treatment fluids.

Aqueous peracetic acid has a distinct advantage as an antimicrobial agent for subterranean well processing operations involving oil- and gas-formations since peracetic acid residues, namely, acetic acid and hydrogen peroxide (which decomposes into $O_2$ and water) are considered environmentally friendly residues.

Peracetic Acid Background

Commercial formulations of aqueous peracetic acid, as noted earlier, not only contain peracetic acid but also hydrogen peroxide, the latter normally in excess of the peracetic acid concentration, and acetic acid in a dynamic chemical equilibrium, as shown in reaction (2) below.

This dynamic equilibrium between peracetic acid, acetic acid, hydrogen peroxide and water in commercial aqueous peracetic acid formulations is essential for maintaining the peracetic acid stability and concentration in such solutions.

Commercial peracetic acid solutions normally contain a concentration of hydrogen peroxide in excess of the peracetic acid concentration, examples being Persan® peracetic acids (Enviro Tech Chemical Services, Modesto Calif.), Peraclean® and Degaclean® peracetic acids (Evonik Industries, Essen, Germany), Proxitane®, Oxystrong® and Perestane® peracetic acids (Solvay S.A., Cheshire, United Kingdom) and Peracetic Acid 5% and Peracetic Acid 15% (15/23) (FMC Corporation, Philadelphia, Pa.).

Commercial formulations of peracetic acid that contain an excess of peracetic acid, as compared to the hydrogen peroxide also present, are relatively uncommon, and known products have been available only in the last ten years, e.g., Peracetic Acid 15% (15/10) and Peracetic Acid 35% (FMC Corporation, Philadelphia, Pa.).

Some references in the prior art to commercial peracetic acid solutions state a specific peracetic acid concentration but make no mention of other chemical components. It should be understood the such prior art peracetic acid solutions must also contain hydrogen peroxide and acetic acid, even though these latter two components are not explicitly mentioned, since aqueous peracetic acid seeks a dynamic equilibrium with hydrogen peroxide and acetic acid, according to reaction (2) above.

The inventors have surprisingly and unexpectedly discovered that certain aqueous peracetic acid solution compositions are suitable for use with polymer-containing aqueous fluids employed in subterranean oil- and gas field operations.

Aqueous peracetic acid solutions in which the hydrogen peroxide concentration is maintained at a reduced level, i.e., at hydrogen peroxide concentrations less than that of the peracetic acid in such solutions, are unexpectedly useful as biocidal compositions for polymer-containing aqueous well fluids. These reduced-$H_2O_2$ aqueous peracetic acid solutions are excellent biocides for aqueous well treatment fluids but are not deleterious to the viscosity-modifying polymers that are normally present in commercial aqueous fluids employed in oil- and gas-field operations.

Peracid Concentration; Use/Treatment Methods

The peracetic acid and peracid biocides of this invention provide effective antimicrobial activity at relatively low concentrations, a distinct economic advantage for well treatment fluids which are typically used in huge volumes.

The concentration of peracetic acid or other peracids of this invention in the aqueous well treatment fluid is normally used within the range of about 1 ppm to about 1000 ppm (0.1 wt %), particularly at the lower concentrations within this range. The preferred concentration range employed with the peracid biocides of this invention is about 1 ppm to about 100 ppm, a more preferred range is about 1 ppm to about 50 ppm, and a most preferred range is about 1 ppm to about 30 ppm. These concentration ranges are based on the weight of the aqueous well fluid composition.

The peracetic acid biocides of this invention provide excellent antimicrobial activity at relatively low concentrations. When maintained within the more preferred concentration range of about 1 ppm to about 50 ppm peracetic acid, and most preferably not more than about 30 ppm, the peracetic acid concentration will normally provide excellent antimicrobial activity against a broad range of microorganisms. At the same time, these low peracetic acid biocide usage levels ensure that the level of hydrogen peroxide oxidant also present (at a concentration less than that of the peracetic acid) is also very low, so that the viscosity-modifying polymer will not be adversely affected by the presence of the hydrogen peroxide that is present along with the peracetic acid. This is generally true regardless of the temperature and pH conditions that the aqueous well treatment fluid may be subjected to in the course of treatment operations.

Concentrations of higher than the preferred upper limit of 100 ppm peracetic acid or other peracid may occasionally be needed and desirable where the aqueous well fluid is known to be highly contaminated with microorganisms, e.g., the fluid having been prepared with a "dirty" or impure water source. In such cases, the concentration of peracid used may even exceed 1000 ppm peracetic acid, but often such high peracid concentrations need only be used once or on an intermittent basis.

Concentrations of peracetic acid or other peracid higher than the preferred upper limit of 100 ppm peracetic acid or other peracid, or even above 50 ppm under some circumstances, may cause some decrease in the viscosity of viscosity-increasing polymers but such decreases are generally not considered to be seriously objectionable. High temperatures in the well formation environment, e.g., above 80° C., can also result in a similar decrease in polymer effectiveness. Such decreases in viscosity-modifying properties may be compensated by adjusting (increasing) the amount of viscosity-modifying polymer employed. Such decreases in viscosity-modifying property provided by the polymer are typically encountered more often with linear polysaccharides like guar than with synthetic polymers like polyacrylamide.

The method by which the peracetic acid or other peracid is introduced into the aqueous well treatment fluid, to provide the desired peracid concentrations, is not critical. Introduction of the peracid may be carried out as a continuous addition or may be intermittent, e.g., slug dose addition. The peracid is preferably added indirectly to the aqueous well fluid composition via one or more of the fluid's components, e.g., the water source, used to prepare the aqueous well fluid composition. The peracid may alternatively be added directly to the well treatment composition. Since concentrated peracid formulations are normally used to provide the desired dilute peracid concentration in the aqueous well treatment fluid, such concentrated peracid should not be added directly to any fluid additive or component with which it may react in such concentrated form.

A preferred method of addition of the peracid is either to the water source used to prepare the aqueous well treatment fluid composition or to the water used (in the case of polymers like guar or guar derivatives) to hydrolyze the polymer. The latter method of addition is particularly favored since the pH of the hydrolysis process step is typically around 5, which is conducive to excellent antimicrobial activity by the peracetic acid or other peracid biocide. In subsequent process operations, other components are often added to the aqueous well treatment fluid that may shift the pH into the highly alkaline region, which is less favorable to antimicrobial activity.

The peracetic acid or other peracid will typically be used in the form of a commercially-available concentrated formulation, e.g., 15 wt % peracetic acid also containing 10 wt % hydrogen peroxide in a stabilized equilibrated aqueous solution. A sufficient amount of the concentrated peracid solution is added to the aqueous well treatment fluid to provide the desired concentration, e.g., within the preferred concentration range of about 1 ppm to about 100 ppm peracid.

Particularly preferred for use in the present invention are 15% (15/10) Peracetic Acid (containing 15 wt % peracetic acid and 10 wt % hydrogen peroxide) and 35% Peracetic Acid (containing about 35 wt % peracetic acid and about 7 wt % hydrogen peroxide), both being commercial peracetic acid formulations available from FMC Corporation (Philadelphia, Pa.). These peracetic acid formulations may be diluted to prepare the peraceti c acid concentrations, with low hydrogen peroxide concentrations, required in the present invention.

Peracid Stabilizers

Aqueous peracetic acid solutions are susceptible to decomposition, particularly at elevated temperatures, at alkaline pH values and in the presence of impurities, e.g., transition metal ions. The stability of aqueous peracetic acid solutions and other peracid solutions is typically improved by the addition of known hydrogen peroxide or peracid stabilizers. Stabilizers used for stabilization of peracid solutions include pyrophosphoric acid or a pyrophosphate (U.S. Pat. No. 2,347,434 of Reichert et al.), phosphates (U.S. Pat. No. 2,590,856 of Greenspan et al.), phosphonates (GB 925 373 of Henkel GmbH), dipicolinic acid (U.S. Pat. No. 2,609,391 of Greenspan et al.), and tin compounds that are preferably stannates (EP-B1-0 563 584 of Degussa AG).

Commercially-available aqueous peracetic acid and other peracid formulations typically contain or more stabilizers such as those described above, so no additional stabilization is required for their use in the preparation of the dilute peracid- or peracetic acid-containing biocidal aqueous well treatment fluids of this invention.

Temperature and pH

The temperature at which the peracid- or peracetic acid-containing biocidal aqueous well treatment fluids of this invention are used in well treatment operations is not critical. Temperatures at which the aqueous well treatment fluid may be used in this invention can vary from about 0° C. to about 130° C. Temperatures in the range of about 5° C. to about 80° C. are preferred, with about 10° C. to about 60° C. being most preferred, for the initial introduction of the peracid biocide to the aqueous well treatment fluid. Since much of the antimicrobial activity of the biocides of this invention is achieved or otherwise effected in a relatively short period of time, long term exposure of the aqueous well treatment fluid to very high subterranean deposit temperatures (e.g., above about 100° C.) is normally not an issue.

Commonly available commercial formulations of peracetic acid typically exhibit a pH of about 1-3 when diluted to a 1 wt % solution. However, no pH adjustment is normally required when such peracetic acid formulations are employed in the preparation of the biocidal aqueous well treatment fluids of this invention.

The pH value of peracetic acid- or other peracid-containing biocidal aqueous well treatment fluids of this invention can range from acidic to slightly alkaline depending on the various additives present in the polymer-containing fluid composition. The pH of the aqueous well treatment fluid is preferably maintained at a pH value of less than about 8 during the time that biocidal activity is desired, since the pKa (negative logarithm of the acid dissociation constant Ka) of peracetic acid is about 8.2 (at 25° C.). Antimicrobial activity of the peracid biocides of this invention is much less effective above pH 8.2. For this reason, the preferred pH range for addition of the peracid biocide to the aqueous well treatment fluids of this invention is about pH 2 to about pH 7.

Contact Time

In the present invention, the length of time that the peracid biocide is in contact with the aqueous well fluid is normally not critical. The contact time, also called exposure time or residence time, is the time that the biocide is in contact with the aqueous well fluid and available to provide biocidal activity. The contact time is normally lengthy since the aqueous fluid is introduced into a subterranean environment where it resides for hours or days, rather than minutes.

Contact times sufficient to provide effective biocidal activity in the aqueous well fluid may range from minutes (e.g., 10 minutes, 30 minutes, 60 minutes) to hours (e.g., 1 hour 12 hours, 24 hours). The choice of an appropriate contact time will depend on factors such as the peracid concentration, microorganism types and colony densities, aqueous fluid temperature and pH, and the like. For example, use of low peracid concentrations, e.g., 50 ppm or less, will typically require longer contact times than use of more concentrated peracid, e.g., 100 ppm or more, to effect the same biocidal activity under otherwise equivalent treatment conditions.

Peracids and Peracid Mixtures

Peracetic acid is the preferred peracid for use in the present invention since its antimicrobial properties are broad spectrum and its residues present no environmental issues. However, other percarboxylic acids besides peracetic acid are also suitable for use in this invention.

A preferred category of suitable organic peracids includes peracids of a lower organic aliphatic monocarboxylic acid having 2-5 carbon atoms, such as acetic acid (ethanoic acid), propionic acid (propanoic acid), butyric acid (butanoic acid), iso-butyric acid (2-methyl-propanoic acid), valeric acid (pentanoic acid), 2-methyl-butanoic acid, iso-valeric acid (3-methyl-butanoic) and 2,2-dimethyl-propanoic acid. Organic aliphatic peracids having 2 or 3 carbon atoms, e.g., peracetic acid and peroxypropanoic acid, are most preferred for the present invention.

Peracetic acid may also be used in combination with other percarboxylic acids based on carboxylic acids other than the monocarboxylic $C_2$-$C_5$ peracids mentioned above, such as $C_2$-$C_5$ dicarboxylic peracids or $C_6$-$C_{12}$ monocarboxylic peracids. Peracetic acid is preferably the major component in such mixtures with higher percarboxylic acids, more preferably being at least about 80 wt % to about 90 wt % of the peracid mixtures.

Peracetic acid may be used in combination with preferred percarboxylic acids selected from the group consisting of peroctanoic acid, perglutaric acid, persuccinic acid, perdecanoic acid and mixtures thereof, to provide good antimicrobial activity in the presence of high organic loads. Peroctanoic acid is the most preferred percarboxylic acid for use in combination with peracetic acid.

Microorganisms

The peracetic acid and other peracid biocides of this invention are noteworthy for their broad spectrum activity against many types of microorganisms and also for their persistence in the aqueous systems being treated. The peracid biocides of this invention provide inhibition, antimicrobial control or killing of the microorganisms for effective microorganism control, so that the deleterious effects of microorganism growth left unchecked in the well treatment fluid is avoided or minimized. Very low concentration levels of the biocide are normally sufficient to provide effective inhibition of microorganism growth or biocidal activity, with the exact amounts or concentration ranges depending of the particular types and amounts of microorganism(s) being controlled and other factors such as pH and temperature of the aqueous well treatment fluid.

The peracetic acid and other peracids of this invention have been found to provide quick and effective antimicrobial activity in relatively short time periods, within minutes or hours rather than days, even when used at dilute concentrations in the aqueous well treatment fluids.

Very dilute concentrations, e.g., 1 ppm to about 10 ppm, of the peracids of this invention provide effective antimicrobial activity in the aqueous well treatment fluids by providing, at a minimum, biostatic activity if not completely killing the microorganisms. Biostatic activity provides effective inhibition and/or regulation and/or control of the growth of microorganisms in the aqueous well treatment fluids. For purposes of this disclosure, the terms biocidal and biocide are intended to encompass both biostatic and biocidal activity provided by the peracetic acid and other peracids of this invention, since both activities provide effective antimicrobial control of microorganisms in the polymer-containing aqueous well treatment fluids of this invention.

The peracids of this invention, in particular the preferred peracetic acid, are not only compatible with the viscosity-modifying polymers used in aqueous well treatment fluids but also with the various other chemical and non-chemical additives that are also present in such fluids. In addition, the peracetic acid and other peracids of this invention are economical to use, since relatively small concentrations provide good biocidal activity, an important consideration in well treatment operations where huge volumes (millions of gallons) of aqueous well treatment fluids are employed.

The peracetic acid and other peracid biocides of this invention are broad spectrum in their antimicrobial activity against wide range of different types of microorganisms. The biocides are active against bacteria, yeasts, molds, fungi, algae, and other problematic microorganisms associated with oil- and gas-field operations using aqueous well treatment fluids. The peracetic acid biocide of this invention is effective against both aerobic microorganisms and anaerobic microorganisms.

Among the microorganisms that are susceptible to treatment with the peracetic acid and other peracids of the present invention are gram positive bacteria, e.g., *Staphylococcus aureus, Bacillus* species (sp.) like *Bacillus subtilis, Clostridia* sp.;

gram negative bacteria, e.g., *Escherichia coli, Pseudomonas* sp. like *Pseudomonas aeruginosa* and *Pseudomonas fluorescens, Klebsiella pneumoniae, Legionella pneumophila, Enterobacter* sp. like *Enterobacter aerogenes, Serratia* sp. like *Serratia marcesens, Desulfovibrio* sp. like *Desulfovibrio desulfuricans* and *Desulfovibrio salexigens, Desulfotomaculum* sp. like *Desulfotomaculum nigrificans;* yeasts, e.g., *Saccharomyces cerevisiae, Candida albicans;* molds, e.g., *Aspergillus niger, Cephalosporium acremonium, Penicillium notatum, Aureobasidium pullulans;* filamentous fungi, e.g., *Aspergillus niger, Cladosporium resinae;* algae, e.g., *Chlorella vulgaris, Euglena gracilis, Selenastrum capricornutum;* and other analogous microorganisms and unicellular organisms, e.g., phytoplankton and protozoa.

Particularly problematic microorganisms in subterranean well treatment operations are the sulfur- or sulfate-reducing bacteria, e.g., *Desulfovibrio* and *Desulfotomaculum* species, which convert sulfur or sulfates present in such environments into sulfides, particularly hydrogen sulfide, a cause of souring in gas and oil products that are recovered from the formation. Such gas or oil souring is considered to be undesirable contamination that reduces the quality of the recovered product, since the sulfides typically need to be removed by chemical treatment of the petroleum product in downstream surface treatment processing.

Sulfur- or sulfate-reducing bacteria, e.g., *Desulfovibrio* and *Desulfotomaculum* species, are an acute problem in aqueous fluids introduced into oil- and gas-field formations, since they are not easily treated with biocides. Sulfate-reducing bacteria are normally sessile bacteria, i.e., they attach themselves to solid surfaces, as opposed to being free-floating in the aqueous fluid. In addition, sulfate-reducing bacteria are generally found in combination with slime-forming bacteria, in films consisting of a biopolymer matrix embedded with bacteria. The interior of these biofilms is anaerobic, which is highly conducive to the growth of sulfate-reducing bacteria even if the surrounding environment is aerobic. Thus, biocides used to treat such environments are presented with the challenge of having to migrate into or penetrate these biofilms, in order to effectively deactivate the problematic bacteria present there.

The peracid biocides of the present invention provide significant advantages over the prior art biocides now used in oil- and gas-field well fluid operations. Control of sulfate-reducing microorganism in well formation environments is presently and conventionally achieved by chemical means, typically using glutaraldehyde as a biocide in the well treatment fluid. Glutaraldehyde, a 5-carbon dialdehyde, is non-oxidizing biocide, known to be effective in inhibiting sulfate-reducing bacteria, and is typically used at concentrations of about 100 to about 2000 ppm.

Other biocides that have been used for this purpose include acrolein, formaldehyde and their derivatives. Acrolein (systemic name 2-propenal) is an aldehyde biocide that is typically used at concentrations of about 1-15 ppm. Formaldehyde (systemic name methanal) is another aldehyde biocide and is typically used at concentrations of about 100 to about 2000 ppm. These traditional aldehyde well fluid biocides introduce undesirable chemicals, or chemical residues, into the subterranean well formation environment and are also hazardous to handle.

Isothiazolinon-derived biocides like methylisothiazolinones and their derivatives (e.g., 5-chloro-2-methyl-4-isothiazolin-3-one, 2-methyl-4-isothiazolin-3-one and their mixtures) have also been used in oil- and gas-field biocide applications, but, like aldehyde-based biocides, isothiazolinones are hazardous to handle and introduce chemical residues into the well formation that raise environmental concerns.

The broad spectrum activity of the peracetic acid and other peracids of this invention against a variety of microorganisms, both aerobic and anaerobic, is important for biocides used in oil- and gas-field well operations. First, biocidal activity is important in the subterranean environment (largely anaerobic) in which the aqueous well treatment fluids are employed, where sulfur-reducing bacteria and other microorganisms can thrive, leading to souring (sulfide contamination) and other microbial contamination of the hydrocarbon products being recovered.

Secondly, biocidal activity is also important in the surface treatment (an aerobic environment) of the water or other aqueous medium used to prepare the aqueous well treatment fluid. The latter water sources are typically impure, often being contaminated with organic, inorganic and biological impurities, allowing the microorganisms to flourish unless treated with a suitable biocide.

Polymers Used in Commercial Well Fluids

The aqueous peracetic acid biocide of the present invention is intended for use with aqueous treatment fluids that are conventionally used in subterranean oil- and gas-field well operations, such as well drilling, formation fracturing, productivity enhancement, secondary recovery and the like. The aqueous well treatment fluids employed in the present invention are characterized by containing one or more viscosity-modifying polymers.

Friction Reducers

In one embodiment of the invention, the viscosity-modifying polymer may function or serve to reduce the fluid viscosity and reduce the flowing friction or reduce flow turbulence, to improve flow characteristics of the aqueous well treatment fluid. Viscosity-reducing polymeric agents are employed in amounts that provide friction-reducing functionality in the aqueous fluid.

Viscosity-reducing polymers are typically used in amounts of about 0.01 to about 1 wt %, more preferably about 0.05 to about 0.5 wt %, based on the weight of the aqueous fluid. A friction-reduced well fluid typically contains an amount of viscosity-reducing polymer sufficient to provide a fluid viscosity of about 10 centipoise (cp) or less, preferably less than about 5 cp (pure water has a viscosity of about 1 cp).

Viscosity Enhancers

In another embodiment of the invention, the viscosity-modifying polymer may alternatively function or serve to increase the fluid viscosity or promote a viscous or semi-gelled or gelled state in the aqueous well treatment fluid. Viscosity-increasing polymeric agents are employed in amounts that provide viscosity-increasing functionality in the aqueous fluid.

Viscosity-increasing polymers are typically used in amounts of about 0.01 to about 10 wt %, more preferably about 0.1 to about 5 wt %, based on the weight of the aqueous fluid. A viscosity-enhanced well fluid typically contains an amount of viscosity-enhancing polymer sufficient to provide a fluid viscosity in excess of 20 cp, more preferably an enhanced viscosity of at least about 50 cp or more.

Examples of Viscosity-Modifying Polymers

The viscosity-modifying polymer may be any of known polymers or copolymers that are typically used in commercial well treatment aqueous fluid compositions. The polymers may be natural polymers, including modified forms of natural polymers, or synthetic polymers, including synthetic polymers and copolymers and their derivatives. The viscosity-modifying polymers are preferably water-soluble, at the concentrations employed in the aqueous well treatment fluids.

A suitable viscosity-modifying polymer, as will be evident from the examples listed below, serve either to reduce viscosity (as a friction-reducer) or to enhance viscosity (as a thickener or gelling agent), depending on the concentration of polymer employed in the aqueous well treatment fluid. As a general rule, dilute concentrations of a viscosity-modifying polymer provide viscosity-reducing functionality in an aqueous well treatment fluid and higher concentrations of the same polymer provide viscosity-enhancement.

Examples of Friction Reducers

Examples of viscosity-reducing polymers that can serve as friction reducers include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamides, acrylamide-methyl-propane sulfonate copolymers (AMPS) and the like. Various derivatives of such polymers and copolymers, e.g., quaternary amine salts, hydrolyzed versions, and the like, should be understood to be included with the polymer and copolymer categories defined in this specification.

Examples of commercial acrylamide-based polymer products that have friction-reducing functionality include NewDrill® products (Baker Hughes, Houston, Tex.), FRW-15 friction reducer (BJ Services, Houston, Tex.), and FR-56" friction reducer (Halliburton, Houston, Tex.). Acrylamide-based polymers and copolymers have also been described in the patent literature for use as friction reducers in oil-field applications such as well fracturing, e.g., U.S. Pat. No. 3,254,719 of Root (Dow Chemical) and U.S. Pat. No. 4,152,274 of Phillips et al. (Nalco Chemical).

Examples of other viscosity-reducing polymers (besides acrylamide-derived polymers and copolymers) that can serve as friction reducers include guar and guar derivatives, acrylate-derived polymers and copolymers like polymethylmethacrylate, ethylene oxide-derived polymers like polyethyleneoxide, alkoxylated alkanolamides, and other biopolymers or synthetic polymers or copolymers that exhibit viscosity-reducing or friction-reducing functionality, and combinations of these.

The so-called slick water well treatment fluids are used for formation fracturing and are typically water containing one or more friction reducers. Slick water well treatment fluids are introduced at very high flow rates into the region of an oil- or gas-bearing formation to fracture the formation, thereby enhancing petroleum product recovery. The preferred friction-reducing polymers in slick water fluids are polyacrylamide or other acrylamide-derived polymers or copolymers, which improve the flow characteristics of the slick water fluid. The peracetic acid biocide of this invention is well suited for providing biocidal activity to slick water well treatment fluids, since such microorganism control is effective not only above-ground but also in the subterranean formation.

Examples of Viscosity Enhancers

Viscosity-increasing polymers or copolymers are used to promote formation of a viscous or semi-gelled or gelled state, usually reversible, in aqueous well treatment fluids. End use applications for such viscosity-enhancing well fluids include inhibition or control flow of water or formation gas and/or oil products flow into the well bore, as well as facilitating uniform dispersal or suspension of various solids used during well operations.

Use of such solids requires that the aqueous well fluid provide sufficient suspension of the solids to ensure that the solids are properly delivered to the site of the well bore or formation where their functionality is needed. Well fracturing procedures using proppants, e.g., inorganic solids like sand, silica, quartz, diatomaceous earth, in coated or uncoated form, require that these solids be suspended in the fluid, delivered and uniformly dispersed throughout the formation fractures by the well fluid during fracturing operations, so a viscous, thickened or partially gelled well fluid is usually employed. In addition, such well fluids often carry other solids, e.g., so-called viscosity breakers, that are employed in well fracturing or other procedures used in gas- and oil-field operations.

Examples of viscosity-enhancing polymers that can serve to increase the fluid viscosity include synthetic polymers such as acrylamide-derived polymers and copolymers and acrylate-derived polymers and copolymers, often in crosslinked form.

Acrylamide-derived polymers and copolymers that can serve as viscosity-enhancing polymers include polyacrylamide, acrylamide-acrylate (acrylic acid) copolymers, acrylic acid-methacrylamide copolymers, partially hydrolyzed polyacrylamide copolymers (PHPA), partially hydrolyzed polymethacrylamides, acrylamide-methyl-propane sulfonate copolymers (AMPS) and the like.

Cross-linked acrylamide-based polymers that exhibit viscosity-enhancing functionality have been described in U.S. Pat. No. 4,995,461 of Sydansk (Marathon Oil) and in U.S. Pat. No. 5,268,112 of Hutchins et al. (Union Oil of California).

Examples of other viscosity-enhancing polymers (besides acrylamide-derived and acrylate-derived polymers and copolymers) that can serve to increase the fluid viscosity include natural and synthetic water-soluble polysaccharides, including guar and guar derivatives such as hydroxypropyl guar and carboxymethyl hydroxypropyl guar; xanthan and xanthan derivatives; alginates and alginate derivatives; carrageenan; cellulosic polymers and cellulosic derivatives such as hydroxyethylcellulose, hydroxypropylcellulose and carboxymethylhydroxyethylcellulose; and other biopolymers or synthetic polymers or copolymers that exhibit gelling or viscosity-enhancing functionality, and combinations of these. These polymers may either be linear (non-crosslinked) or crosslinked, e.g., using cross-linking agents such as borate or zirconate or titanate.

Other Fluid Additives/"Fluid"

The aqueous well treatment fluids employed in the present invention may contain other components or additives besides the viscosity-modifying polymer and the peracetic acid or other peracid biocide of this invention. Such components or additives may include emulsifiers, anti-scale agents, surfactants, proppants, viscosity breaking agents, antifoaming or foaming agents, storage stabilizers and other like components that may be used in conventional aqueous well treatment fluids.

The term fluid as used in reference to the term well treatment fluid employed in this invention should be understood to refer to an aqueous medium that may be an aqueous solution, an aqueous suspension (aqueous medium with solids and/or gas), a thickened or partially gelled but pumpable aqueous medium, or like fluid that can be introduced via a well bore hole to a subterranean formation.

The aqueous medium used in the preparation of the aqueous well treatment fluid containing a viscosity-modifying polymer is normally water. The water source may be a freshwater source, salt water or brine source, brackish water source, recycled water source, or the like. Offshore well drilling operations typically employ seawater, whether saltwater or not, and the biocide of the present invention is useful for treating well fluids derived from any of these sources.

Since extremely large volumes of water are typically required in well fluid operations, economic constraints often dictate the use of recycled water, brine water or non-potable water sources. One advantage of the peracid or peracetic acid biocide of the present invention is its ability to inhibit or otherwise control the growth of microorganisms that may be present in such water sources.

EXAMPLES

The following non-limiting Examples 1 and 2 illustrate preferred embodiments of the present invention.

Example 1

Example 1 illustrates the biocidal efficacy of peracetic acid, compared with glutaraldehyde, against a strain of sulfur-reducing bacteria, *Desulfovibrio desulfuricans* (*vulgaris*), present in an aqueous solution also containing 0.1 wt % polyacrylamide polymer. A range of peracetic acid and glutaraldehyde concentrations were evaluated for biocidal efficacy: 5, 10, 30, 150 and 300 ppm peracetic acid and 25 and 500 ppm glutaraldehyde.

The dilute aqueous polyacrylamide was prepared using a 50 wt % polyacrylamide solution in water, with the polyacrylamide having an average molecular weight ~10,000 (Aldrich No. 434949, Sigma-Aldrich, St. Louis, Mo.). The peracetic acid was Vigor Ox® SP-15 antimicrobial agent, containing about 15-17 wt % peracetic acid, 9-11 wt % hydrogen peroxide and 33-38 wt % acetic acid in water (FMC Corporation, Philadelphia, Pa.), and this peracetic acid solution was diluted to 5, 10, 30, 150 and 300 ppm peracetic acid for the various evaluations. The glutaraldehyde used in this Example 1 was a 25 wt % glutaraldehyde solution in water (Sigma-Aldrich No. G4004, Sigma-Aldrich, St. Louis, Mo.), diluted to either 25 or 500 ppm for the evaluations.

The bacterial strain, *Desulfovibrio desulfuricans* (*vulgaris*) (ATCC 7757 from American Type Culture Collection, Manassas, Va.), was introduced to a substrate of the 0.1 wt % polyacrylamide in aqueous solution, and the peracetic acid or glutaraldehyde was then added to the desired concentration. The incubated vessels maintained at an incubation temperature of 22° C., 45° C. or 80° C. in an anaerobic atmosphere and were sampled at various time points, e.g., 24 hours, 48 hours, 5 days, to ascertain bacteria colony survival at the time point. The incubation samples were plated and cultured/grown on sulfate API agar growth medium at ambient temperature to determine the colony forming units (CFU).

Controls

Controls were also carried out, in which *Desulfovibrio vulgaris* was introduced into two aqueous media, one containing deionized water alone and the second containing 0.1 wt % polyacrylamide in deionized water. The initial inoculation level was $1.6 \times 10^6$ CFU/tube.

The two aqueous solutions were incubated at a temperature of 22° C. and sampled for colony analysis at 24 hours and five days. The control samples containing the bacterium in water alone (pH 6.9) analyzed as $4.0 \times 10^5$ CFU at 24 hours and <100 CFU at five days. A repeat test sample (initial inoculation level of $1.4 \times 10^6$ CFU/tube) analyzed as $6.5 \times 10^5$ CFU at 24 hours and $1.5 \times 10^5$ CFU at 48 hours (no analysis at five days).

The control samples containing the bacterium in 0.1 wt % polyacrylamide in water (pH 5.5) analyzed as $6.5 \times 10^5$ CFU at 24 hours and $1.0 \times 10^5$ CFU at five days. A repeat test sample (initial inoculation level of $1.4 \times 10^6$ CFU/tube) analyzed as $3.5 \times 10^5$ CFU at 24 hours and $1.5 \times 10^5$ CFU at 48 hours (no analysis at five days). These results, when compared with the control sample results for deionized water without polyacrylamide, indicate that survival of the *Desulfovibrio vulgaris* bacterium populations requires a nutrient source such as provided in the 0.1 wt % polyacrylamide aqueous medium.

Similar control tests were also performed at higher incubation temperatures (37° C. and 45° C.), but in each case the *Desulfovibrio vulgaris* bacterium populations did not survive beyond 24 hours, suggesting that this organism is sensitive to elevated temperatures, even when a nutrient source (0.1 wt % polyacrylamide) is present.

Peracetic Acid and Glutaraldehyde

Peracetic acid and glutaraldehyde were next evaluated for biocidal efficacy against the sulfur-reducing bacterium *Desulfovibrio vulgaris*. For the peracetic acid study, samples of aqueous solution containing 0.1 wt % polyacrylamide and inoculated with *Desulfovibrio vulgaris* bacterium were treated with peracetic acid at various treatment dosages and temperatures: 5 ppm, T=22° C. (pH 5.9); 10 ppm, T=22° C. (pH 4.9); 10 ppm, T=22° C. (pH 8.5); 30 ppm, T=45° C. (pH 4.2); 150 ppm, T=45° C. (pH 4.2); 150 ppm, T=45° C. (pH 8.5); and 300 ppm, T=80° C. (pH 2.8).

In a limited comparison study using glutaraldehyde as the treatment agent, samples of aqueous solution containing 0.1 wt % polyacrylamide and inoculated with *Desulfovibrio vulgaris* bacterium were treated with glutaraldehyde at various treatment dosages and temperatures: 25 ppm, T=22° C. and 80° C.; 500 ppm, T=22° C. and 80° C.

For all of the peracetic acid-treated samples (5 & 10 ppm @ 22° C.; 30 & 50 ppm @ 45° C.; 300 ppm @ 80° C.) and likewise for the glutaraldehyde-treated samples (25 & 500 ppm @ 22° C. & 80° C.), colony population analysis at 24 hours and beyond showed essentially complete removal (>99.99% reduction) of the *Desulfovibrio vulgaris* bacterium in each of the samples at each of the dosages and temperatures evaluated.

In this Example, the peracetic acid biocidal efficacy against *Desulfovibrio vulgaris* was demonstrated over a wide range of peracetic acid concentrations. Although not a side-by-side comparative study (since only two concentrations and temperatures were evaluated for the glutaraldehyde treatment), peracetic acid biocidal efficacy against *D. vulgaris* was also demonstrated to be at least equivalent in performance to the glutaraldehyde treatment.

Example 2

Example 2 illustrates the biocidal efficacy of peracetic acid, compared with glutaraldehyde, against another strain of sulfur-reducing bacteria, *Desulfotomaculum nigrificans*, present in an aqueous solution also containing 0.1 wt % polyacrylamide polymer. A range of peracetic acid and glutaraldehyde concentrations were evaluated for biocidal efficacy: 1, 5, 10, 25, 50, 75, 100, 200 and 300 ppm peracetic acid and the same concentrations for glutaraldehyde (except that 300 ppm was omitted).

The dilute aqueous polyacrylamide was prepared using an aqueous 50 wt % polyacrylamide solution (Sigma-Aldrich, St. Louis, Mo.) and diluting the polyacrylamide with deionized water to obtain 0.1 wt % polyacrylamide in water. The peracetic acid was Vigor Ox® SP-15 antimicrobial agent, containing about 15-17 wt % peracetic acid, 9-11 wt % hydrogen peroxide and 33-38 wt % acetic acid in water (FMC Corporation, Philadelphia, Pa.), and this peracetic acid solution was diluted to the desired concentration within the range 1 to 300 ppm peracetic acid for the various evaluations. The glutaraldehyde used in this Example 2 was a 50 wt % glutaraldehyde solution in water (Alfa Aesar, Ward Hill, Mass.), diluted with deionized water to the desired concentration within the range 1 to 200 ppm for the evaluations.

The bacterial strain used in this Example 2 was the sulfur-reducing bacterium *Desulfotomaculum nigrificans* (ATCC 19858 from American Type Culture Collection, Manassas, Va.). A working inoculum for each of the three studies described below was prepared by the following procedure. Baar's medium for sulfate reducers was inoculated with *D. nigrificans* from a cryogenic tube, grown at 50° C. anaerobically for a period sufficient to observe good growth of the culture (evident by blackening of the tube), between 2-7 days. This *D. nigrificans* culture was used as the working inoculum for each of the studies described below.

Methodology

The methodology used in this Example 2 was as follows. A sterilized screw-cap tube containing 9.5-10 ml 0.1 wt % polyacrylamide was dosed with an appropriate amount of peracetic acid (or glutaraldehyde) to provide the desired peracetic acid (or glutaraldehyde) concentration (e.g., 1 to 300 ppm peracetic acid) in 10 ml 0.1 wt % polyacrylamide required for the study. The tubes were then vortex mixed and 0.1 ml *D. nigrificans* inoculum was added and again vortex mixed. The initial inoculation level was estimated as about $2.6 \times 10^6$ CFU/tube. Timing of the exposure period (e.g., 1 minute to 1 day) was begun when the *D. nigrificans* inoculum was added.

After the exposure period had elapsed, 1 ml of the treated mixture was added to a second tube containing 9 ml of Dey-Engley (D/E) neutralizing broth and vortex mixed. After about 5-8 minutes had elapsed, 1 ml of the neutralized solution was added to yet another tube containing 9 ml of Baar's modified medium for sulfate reducers. This tube was vortex mixed and then incubated anaerobically at 50° C., with the screw cap loosened, using an AnaeroPack (Mitsubishi Gas Chemical America, Inc., New York, N.Y.) in an anaerobic jar. The tube was examined for growth after two days and final results obtained after 4-5 days (although no changes in the two day growth observation, or not, were observed in this intervening period).

Growth controls were also carried out in the studies of this Example 2, using the following procedure. A screw-cap tube containing 10 ml of 0.1 wt % polyacrylamide was inoculated with 0.1 ml of *D. nigrificans* culture and then diluted in D/E neutralizing broth after the exposure period, vortex mixed, and then diluted in Baar's medium as described above. The control tubes were incubated at 50° C., also as described above, and monitored for growth after two days.

Neutralizing controls were also carried out for the peracetic acid and glutaraldehyde treatment agents to confirm that D/E neutralizing broth (which contains sodium bisulfite and sodium thiosulfate among its neutralizing agents) was capable of neutralizing either peracetic acid or glutaraldehyde at the highest concentration used in each study.

In the neutralizing control procedure, screw-cap tubes containing 0.1 wt % polyacrylamide were dosed with the appropriate amount of treatment agent to prepare tubes at the highest concentration of treatment agent employed in the study. One ml of the solution was then be added to 9 ml of D/E neutralizing broth, and vortex mixed. Next, 0.01 ml of *D. nigrificans* inoculum was added to the neutralizing broth in the tube to approximate the starting titer in the study. The tube was vortex mixed once again, and a 1 ml aliquot of the neutralized inoculated solution was added to another tube containing 9 ml of Baar's medium, vortex mixed, the cap loosened, and then incubated along with the other tubes in the study.

Peracetic Acid and Glutaraldehyde Studies

In a first study in this Example 2, peracetic acid and glutaraldehyde were used at relatively low to moderate concentrations in treatments of aqueous samples of 0.1 wt % polyacrylamide inoculated with *Desulfotomaculum nigrificans*, to study the biocidal efficacy of such treatments. The study evaluated the biocidal efficacy of peracetic acid in concentrations of 1, 5, 10, 25 and 50 ppm peracetic acid for exposure times (contact times) of about 1 minute, 1 hour and 1 day. In addition and for comparative purposes, the study also evaluated the biocidal efficacy of glutaraldehyde in the same concentrations and for the same exposure times.

The results of the study are summarized in Table 1 below. The Table shows biocide, concentration and *D. nigrificans* growth results for peracetic acid and glutaraldehyde over the concentration ranges (1 ppm to 50 ppm) and exposure times (1 minute, 1 hour and 1 day) used in this first study. Two replicates were performed at each concentration and exposure time. For growth results, the Table indicates "+" for positive growth and "NEG" for negative (no) growth.

TABLE 1

| Biocide | Concentration | *D. nigrificans* Growth Results (positive (+) or negative (NEG)) | | | | | |
|---|---|---|---|---|---|---|---|
| | | 1 minute | | 1 hour | | 1 day | |
| Peracetic Acid | 1 ppm | + | + | + | + | + | + |
| | 5 ppm | + | + | + | + | + | + |
| | 10 ppm | + | + | + | + | + | + |
| | 25 ppm | + | + | + | + | NEG | NEG |
| | 50 ppm | + | + | NEG | + | NEG | NEG |
| Glutaraldehyde | 1 ppm | + | + | + | + | + | + |
| | 5 ppm | + | + | + | + | + | + |
| | 10 ppm | + | + | + | + | + | + |
| | 25 ppm | + | + | + | + | + | + |
| | 50 ppm | + | + | + | + | + | + |
| Growth Control | 0 ppm | + | + | + | + | + | + |
| Peracetic Acid Neutral Control | 50 ppm | + | + | not tested | | not tested | |
| Glutaraldehyde Neutral Control | 50 ppm | + | + | not tested | | not tested | |

As shown in Table 1, no biocidal control of *D. nigrificans* was observed for glutaraldehyde at any of the concentrations or exposure times studied. For the peracetic acid treatment, no biocidal control of *D. nigrificans* was observed at low concentrations of 1 ppm, 5 ppm or 10 ppm at any of the exposure times studied.

However, peracetic acid at the two highest concentrations of 25 ppm and 50 ppm provided biocidal control of *D. nigrificans* ("NEG") at the longest exposure time of 1 day. In addition, the peracetic acid at 50 ppm also provided some biocidal activity after only one hour, as indicated by the "NEG" result for one of the two replicates evaluated at this exposure time.

Table 1 also confirms that the growth control (0 ppm) and neutral controls (50 ppm peracetic acid or glutaraldehyde) exhibited no biocidal activity at the exposures times studied; see last three rows.

In a second study in this Example 2, peracetic acid and glutaraldehyde were used at moderate to high concentrations in treatments of aqueous samples of 0.1 wt % polyacrylamide inoculated with *D. nigrificans*, to study the biocidal efficacy of such treatments. The study evaluated the biocidal efficacy of peracetic acid in concentrations of 50, 75, 100 and 200 ppm peracetic acid for exposure times (contact times) of 10 minutes, 1 hour and 1 day. In addition and for comparative purposes, the study also evaluated the biocidal efficacy of glutaraldehyde in the same concentrations and for the same exposure times.

The results of the study are summarized in Table 2 below. The Table shows biocide, concentration and *D. nigrificans* growth results for peracetic acid and glutaraldehyde over the concentration ranges (50 ppm to 200 ppm) and exposure times (10 minutes, 1 hour and 1 day) used in this second study. As before, two replicates were performed at each concentration and exposure time. For growth results, the Table indicates "+" for positive growth and "NEG" for negative (no) growth.

TABLE 2

| Biocide | Concentration | *D. nigrificans* Growth Results (positive (+) or negative (NEG)) | | | | | |
|---|---|---|---|---|---|---|---|
| | | 10 minutes | | 1 hour | | 1 day | |
| Peracetic Acid | 50 ppm | + | + | + | + | NEG | NEG |
| | 75 ppm | + | + | NEG | NEG | NEG | NEG |
| | 100 ppm | + | + | NEG | + | NEG | NEG |
| | 200 ppm | + | + | NEG | NEG | NEG | NEG |

TABLE 2-continued

| Biocide | Concentration | D. nigrificans Growth Results (positive (+) or negative (NEG)) | | |
|---|---|---|---|---|
| | | 10 minutes | 1 hour | 1 day |
| Glutaraldehyde | 50 ppm | + + | + + | + + |
| | 75 ppm | + + | + + | + + |
| | 100 ppm | + + | + + | + + |
| | 200 ppm | + + | + + | + + |
| Growth Control | 0 ppm | + + | + + | + + |
| Peracetic Acid Neutral Control | 200 ppm | + + | not tested | not tested |
| Glutaraldehyde Neutral Control | 200 ppm | + + | not tested | not tested |

As shown in Table 2, no biocidal control of *D. nigrificans* was observed for glutaraldehyde at any of the concentrations or exposure times studied.

However, peracetic acid at all concentrations studied, 50, 75, 100 and 200 ppm, provided biocidal control of *D. nigrificans* ("NEG") at the longest exposure time of 1 day, as shown by the results in Table 2. In addition, the peracetic acid at only 1 hour exposure time also demonstrated biocidal activity, at 75 ppm, at 100 ppm (for 1 of 2 replicates) and at 200 ppm. At the shortest exposure time of 10 minutes, no biocidal activity was observed for peracetic acid at any of the concentrations studied.

Table 2 also confirms that the growth control (0 ppm) and neutral controls (200 ppm peracetic acid or glutaraldehyde) exhibited no biocidal activity at the exposures times studied; see last three rows.

In a third study in this Example 2, peracetic acid was used at high concentrations in treatments of aqueous samples of 0.1 wt % polyacrylamide inoculated with *D. nigrificans*, to study the biocidal efficacy of such treatments for exposure times up to 1 hour. The study evaluated the biocidal efficacy of peracetic acid in concentrations of 100, 200 and 300 ppm peracetic acid for exposure times (contact times) of 10 minutes, 30 minutes and 60 minutes. In this third study (unlike the first two studies), glutaraldehyde was not included in the testing.

The results of the study are summarized in Table 3 below. The Table shows biocide, concentration and *D. nigrificans* growth results for peracetic acid over the concentration ranges (100 ppm to 300 ppm) and exposure times (10 minutes, 30 minutes and 60 minutes) used in this third study. In this third study, three replicates were performed at each concentration and exposure time. For growth results, the Table indicates "+" for positive growth and "NEG" for negative (no) growth.

TABLE 3

| Biocide | Concentration | D. nigrificans Growth Results (positive (+) or negative (NEG)) | | |
|---|---|---|---|---|
| | | 10 minutes | 30 minutes | 60 minutes |
| Peracetic Acid | 100 ppm | + + + | + NEG NEG | NEG + NEG |
| | 200 ppm | + + + | NEG NEG NEG | NEG NEG NEG |
| | 300 ppm | NEG NEG NEG | NEG NEG NEG | + NEG NEG |
| Growth Control | 0 ppm | + | + | + |
| Peracetic Acid Neutral Control | 300 ppm | + | + | not tested   not tested |

As shown in Table 3, peracetic acid provided biocidal control of *D. nigrificans* ("NEG") at the longest exposure time of 60 minutes at all concentrations studied, using an "all or nothing" classification without regard to log reductions: 100 ppm (2 of 3 replicates), 200 ppm and 300 ppm (2 of 3 replicates). In addition, at a shorter exposure time of 30 minutes peracetic acid also demonstrated biocidal activity, at the three concentrations studied: 100 ppm (2 of 3 replicates), 200 ppm and 300 ppm. At the shortest exposure time of ten minutes, the 300 ppm concentration of peracetic acid exhibited biocidal control, but the lower concentrations (100 and 200 ppm) did not exhibit biocidal activity.

Table 3 also confirms that the growth control (0 ppm) and neutral control (300 ppm peracetic acid) exhibited no biocidal activity at the exposures times studied; see last two rows.

It will be appreciated by those skilled in the art that changes could be made to the embodiments described above without departing from the broad inventive concept thereof. It is understood, therefore, that this invention is not limited to the particular embodiments disclosed but is intended to cover modifications within the spirit and scope of the present invention as defined by the appended claims.

What is claimed is:

1. A method of providing biocidal activity in a well treatment fluid comprising
   introducing, into an aqueous well treatment fluid composition comprising a polymer or copolymer for modifying fluid viscosity, wherein the polymer or copolymer is selected from the group consisting of acrylamide derived polymers and copolymers; acrylate derived polymers and copolymers; guar and guar derivatives; ethylene oxide-derived polymers, and combinations of these, an aqueous peracetic acid solution in an amount sufficient to provide an antimicrobial-effective amount of about 1 ppm to about 1000 ppm peracetic acid, the aqueous peracetic acid solution having a peracetic acid weight concentration of about 15-17 wt % and hydrogen peroxide concentration of about 9-11 wt %; and thereafter
   directing the aqueous well treatment fluid into a subterranean environment susceptible to contamination by sulfur-reducing bacteria.

2. The method of claim 1 wherein the aqueous peracetic acid solution is introduced in an amount sufficient to provide about 1 ppm to about 50 ppm peracetic acid.

3. The method of claim 1 wherein the aqueous peracetic acid solution is introduced into the aqueous well treatment fluid composition when the composition has a pH less than about 8.

4. The method of claim 1 wherein the aqueous peracetic acid solution is introduced into water used to prepare the aqueous well treatment fluid composition.

5. The method of claim 1 wherein the polymer or copolymer serves to reduce fluid viscosity and is present in a friction-reducing amount to provide improved fluid flow characteristics.

6. The method of claim 5 wherein the friction-reducing polymer or copolymer is present in an amount of about 0.01 wt % to about 1 wt %, based on the weight of the aqueous composition.

7. The method of claim 1 wherein the polymer or copolymer serves to increase fluid viscosity and is present in an amount sufficient to provide increased fluid viscosity.

8. The method of claim 7 wherein the viscosity-increasing polymer or copolymer is selected from the group consisting of acrylamide-derived polymers and copolymers; acrylate-derived polymers and copolymers; natural and synthetic polysaccharides and their derivatives; natural and synthetic cellulosic polymers and copolymers and their derivatives; and combinations of these.

9. The method of claim 8 wherein the viscosity-increasing polymer or copolymer is at least partially crosslinked.

10. The method of claim 7 wherein the viscosity-increasing polymer is present in an amount of about 0.1 wt % to about 10 wt %, based on the weight of the aqueous composition.

11. The method of claim 1 wherein the sulfur-reducing bacteria is selected from the group consisting of *Desulfovibrio* species and *Desulfotomaculum* species.

\* \* \* \* \*